US006280729B1

(12) United States Patent
Huang et al.

(10) Patent No.: US 6,280,729 B1
(45) Date of Patent: *Aug. 28, 2001

(54) PREPARATION OF FACTOR IX

(75) Inventors: Chin C. Huang, Bourbonnais; Takashi Enkoji, Park Forest; Laura Ho, Bourbonnais; Richard R. Kleszynski, St. Anne; Richard L. Weeks, Kankakee; Fred Feldman, Frankfort, all of IL (US)

(73) Assignee: Aventis Behring LLC, King of Prussia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/524,206

(22) Filed: Mar. 13, 2000

Related U.S. Application Data

(62) Division of application No. 08/465,867, filed on Jun. 6, 1995, now Pat. No. 6,043,215, which is a division of application No. 08/101,175, filed on Aug. 3, 1993, now Pat. No. 6,063,909, which is a continuation-in-part of application No. 07/662,927, filed on Mar. 1, 1991, now abandoned.

(51) Int. Cl.$^7$ .................................................. A61K 38/48
(52) U.S. Cl. ........................................... 424/94.64; 514/8
(58) Field of Search ............................... 514/8, 381, 384; 424/94.64

(56) References Cited

U.S. PATENT DOCUMENTS

| | | | |
|---|---|---|---|
| 4,379,085 | 4/1983 | Williams et al. | 260/112 B |
| 4,405,603 | 9/1983 | Schwinn et al. | 424/101 |
| 4,411,794 | 10/1983 | Schwinn et al. | 210/670 |
| 4,447,416 | 5/1984 | Menache-Aronson | 424/101 |
| 4,578,216 | 3/1986 | Saundry | 260/112 B |
| 4,687,664 | 8/1987 | Philapitsch et al. | 424/85 |
| 4,725,673 | 2/1988 | Herring | 530/384 |
| 4,770,999 | 9/1988 | Kaufman et al. | 436/68 |
| 4,786,726 | 11/1988 | Smith | 530/381 |
| 4,981,952 | 1/1991 | Yan | 530/384 |
| 5,055,557 | 10/1991 | Zimmerman | 530/381 |
| 5,061,789 | 10/1991 | Moller et al. | 530/381 |
| 5,071,961 | 12/1991 | Kraus et al. | 530/384 |
| 5,281,661 | 1/1994 | Linnau et al. | 525/54.1 |
| 5,457,181 | 10/1995 | Michalski et al. | 530/381 |
| 5,614,500 | 3/1997 | Zimmerman | 514/21 |
| 5,639,857 | 6/1997 | Zimmerman | 530/384 |
| 6,043,215 * | 3/2000 | Huang et al. | 514/8 |
| 6,063,909 * | 3/2000 | Huang et al. | 530/412 |

FOREIGN PATENT DOCUMENTS

| | | |
|---|---|---|
| 0 118 256 | 9/1984 | (EP) . |
| 0251874A1 | 1/1988 | (EP) . |
| 2080312A | 2/1982 | (GB) . |
| 2080312B | 12/1983 | (GB) . |
| 1258700A | 10/1989 | (JP) . |

OTHER PUBLICATIONS

Pool, J.G. et al., *Nature*, 203, 312 (1964).
Kingdon H.S. et al., *Thromb. Diath. Haemorr.*, 33, 617–631(1975).
Miletech, J.P. et al., *J. of Biol. Chem.*, 253(19), 6908–6916 (1978).
Rosenberg et al., *J. Biol. Chem.*, 250, 1607–1617 (1974).
Cash, J.D. et al., *Vox Sang*, 35, 105–110 (1978).
Giles, A.R. et al., *Thrombosis Res.*, 17, 353–366 (1980).
Wessler et al., *J. Applied Physiol.*, 14, 943–946 (1959).
Pasternack et al., *Nature*, 322, 740 (1986).
Laemli, U.K., *Nature*, 227, 680–685 (1970).
Weber, K. et al., *J. Biol. Chem.*, 244, 4406–4412 (1969).
Bloom, J.W. et al., *Biochemistry*, 18, 4419–4425 (1979).
Jallat, S. et al., *EMBO Journal*, 9(10), 3295–3301 (1990).
Anson, D.S. et al., *Nature*, 315:683–685 (1985).
Blatt, P.M. et al., *Annals of Internal Medicine*, 81, 766–770 (1974).
Menache, D. et al., *Blood*, 64(6), 1220–1227 (1984).
Michalski et al., *Vox Sang*, 55, 202–210 (1988).
Goodall, A.H. et al., *Blood*, 59(3), 664–670 (1982).
Liebman, H.A. et al., *Blood*, 62(5), supp. 1, 288a (1983).
Liebman, H.A. et al., *PNAS*, 82, 3879–3883 (1985).
Bessos et al., *Thromb. and Haemos.*, 56(1), 86–89 (1986).
Bajaj, S.P. et al., *Preparative Biochemistry*, 11(4), 397–412 (1981).
Miletech, J.P. et al., *Methods in Enzymology*, 80, 221–228 (1981).
Tharakan, J. et al., *Vox Sang*, 58, 21–29 (1990).
Shapiro, S.S. et al., *Thromb. Diath. Haemorr.*, 16, 469 (1966).
Smith, K.J. et al., *Blood*, 72, 1269–1277 (1988).
Jenny, R. et al., *Preparative Biochemistry*, 16, 227–245 (1986).
Osterud, B. et al., *J. Biol. Chem.*, 253(17), 5946–5951 (1978).
Varadi, K. e al., *Thromb. Haemos.*, 35, 576–585 (1976).
Koehler G. and Milstein, C., *Nature*, 256, 495–497 (1975).
Smith, K.J. et al., *Thromb. Haemostas.*, 58, 349 (1987).
Brown, J.P. et al., *J. Biol. Chem.*, 225, 4980–4983 (1980).
Smith, K.J. et al., *Thrombosis Research*, 33, 211–224 (1984).
Burnouf et al., *Vox Sang.*, 57, 225–232 (1989).
Ahmad et al., *Thrombosis Research*, 55, 121–133 (1989).

\* cited by examiner

*Primary Examiner*—Karen Cochrane Carlson
(74) *Attorney, Agent, or Firm*—Synnestvedt & Lechner LLP

(57) ABSTRACT

A novel method of protecting blood coagulation factor IX from proteases during purification or storage is disclosed. High concentrations of one or more water soluble organic or inorganic salts are used to stabilize factor IX, contained within blood plasma-derived solutions, or contained within solutions derived from other sources, against conversion to clinically unacceptable peptide structures such as factor $IX_a$, and/or degraded factor IX peptides. The technique is useful in stabilizing intermediate purity factor IX preparations during purification, and in maintaining the integrity of purified factor IX during long term storage. Stable high specific activity factor IX preparations are also disclosed.

9 Claims, 4 Drawing Sheets

PREPARATION OF FACTOR IX

RELATED APPLICATIONS

This application is a division of U.S. application Ser. No. 08/465,867, filed Jun. 6, 1995 now U.S. Pat. No. 6,043,215, which is a division of U.S. application Ser. No. 08/101,175, filed Aug. 3, 1993 now U.S. Pat. No. 6,063,909 which is a continuation-in-part of U.S. application Ser. No. 07/662,927, filed Mar. 1, 1991, now abandoned, all of which are incorporated herein by reference.

FIELD OF THE INVENTION

This invention relates to purifying and stabilizing factor IX, one of the proteins essential to the cascade of reactions which accomplishes blood coagulation at the site of a wound.

Factor IX is a globular protein which has a molecular weight of about 70,000 daltons and which, in a normal individual, is constantly produced in the liver and circulates at a normal blood plasma concentration of approximately 5 µg/ml.

Hemophilia B (also known as Christmas disease) is a very serious illness which results in decreased in vivo and in vitro clotting activity and requires extensive medical monitoring throughout the life of the affected person. Such persons show normal clotting times only when provided with exogenous factor IX which is extracted from the blood plasma of normal individuals. Except for such treatment, the afflicted person can suffer from spontaneous bleeds in joints which produce severe pain and debilitating immobility, bleeds into muscles resulting in large volumes of blood accumulating in the tissue, spontaneous bleeds in the throat and neck which may cause asphyxiation if not immediately treated, bleeding into the urine, and severe bleeding following surgery or minor accidental injuries or dental extractions.

Functional factor IX deficiencies can arise in different ways. The gene coding for factor IX is located on the X chromosome. This explains why hemophilia B is much more common in males than females. Some of the afflicted persons are known to have inherited an X chromosome with a complete deletion of the factor IX gene. These severely affected persons may even produce antibodies to therapeutically injected factor IX. Many hemophilia B patients are known to produce a factor IX molecule with an altered amino acid sequence which results in molecules of partial or no coagulation activity. Some hemophilia B patients produce normal factor IX, but in insufficient quantities to effect clotting within a normal time after injury.

As mentioned above, Factor IX activity can be restored in the patient by injection of normal human plasma. However, at minimum, several liters would have to be administered to raise the patients's circulating factor IX levels to an effective range. Accordingly, the emphasis in therapy for hemophilia B patients has been to provide injections of a plasma concentrate highly enriched in factor IX. The provision of such a concentrate is no easy task, as will become apparent from the discussion which follows.

The mechanisms whereby circulating blood is generally prevented from clotting, yet directed to clot at the site of a wound are very complex and involve numerous proteins, other macromolecules, cells and structures. This hemostatic mechanism also utilizes numerous feedback or amplification pathways to further regulate coagulation. Owing to the large number of individual protein species which make up the clotting pathway and the large number of other macromolecules in blood plasma, it is generally difficult to isolate useable quantities of any one component, including factor IX, in highly pure form. In addition, blood contains numerous proteases (enzymes which digest or damage other proteins) which can affect adversely the protein selected for isolation, such as factor IX, before it can be separated from other blood components.

Since the clotting ability of the blood is held in a controlled balance, factor IX and other components associated with coagulation must be held inactive most of the time to avoid unnecessary clotting. Yet, the proteins must always be present throughout the circulatory system—ready to react immediately when needed.

The blood therefore contains by necessity a very complicated mechanism to prevent clotting from taking place where it is not needed, to clear unwanted clotting, and to rapidly stop the loss of blood at an injured site. The elucidation of this complicated mechanism of regulation makes clear why it is so difficult to isolate therapeutic factor IX free of clinically dangerous contaminants.

The formation of an effective clot involves the complex interaction of many vascular system components, including platelet blood cells, collagen and microfibrils exposed by damage to the vascular epithelium, phospholipids, and circulating proteins. Proteins which circulate in the blood as inert proenzymes and which are involved in coagulation are typically referred to as "coagulation factors". Upon activation, they generally function as highly specific enzymes which make specific alterations in other coagulation factor proenzymes. Thus, in turn, each sequential factor is activated. Some proenzymes, such as factor XII, may also be activated by contact with a damaged surface or by complexing with other macromolecules.

The mechanism of the clotting process is known in considerable detail. The active form of a coagulation factor is denoted by the subscript "a" and is typically produced from the inactive proenzyme by the action of another of the factor-specific proteases. In theory, administration of activated coagulation factors to hemophilia patients carries a risk of clot formation at many locations besides the site of injury.

The hemostatic mechanism may be characterized as a very delicate balance between those materials or processes which inhibit coagulation and those which enhance it. Oversupply of one or more substances, particularly activated coagulation factors, may lead to unwanted coagulation. Activated coagulation factors can therefore be dangerous contaminants in therapeutic preparations of coagulation proenzymes, such as factor IX preparations.

With respect to hemophilia B patients, the state of the art, however, involves their being typically treated with "prothrombin complex concentrate", which is a plasma extract concentrated in factor IX, but containing also significant amounts of other plasma proteins, including factors II, VII, X, active forms thereof, and numerous other contaminating proteases. Such preparations can also routinely be contaminated with factor $IX_a$.

There are numerous reports in the literature on the adverse clinical consequences of administering prothrombin complex concentrate (or other factor IX concentrates) contaminated with factor $IX_a$ and/or with active or degraded forms of other clotting factors. The most serious risk is the inadvertent activation of the clotting cascade. Deaths have been documented.

Solutions to the problems associated with the use of impure factor IX concentrates have been hampered by lack of understanding of exactly how and why such concentrates induce unwanted clotting. It has been proposed that factor IX concentrates may induce coagulation not only because amounts of factors $IX_a$ are present, but also because they are significantly contaminated with other clotting factors, thus overloading the blood with high circulating levels of one or more clotting factors, or activated forms thereof.

Based on determinations using sodium dodecylsulfate-polyacrylamide gel electrophoresis (SDS-PAGE), factor $IX_a$ has an approximate molecular weight of 54,000. However, other peptide species which result from proteolytic degradation of factor IX have very similar molecular weights for example, from approximately 40,000 to approximately 65,000. It is not currently known whether factor IX activation products or degradation products are primarily responsible for adverse clinical consequences which have been observed on administration of prothrombin complex concentrate or other impure factor IX-containing concentrates. Consequently, the development of factor IX therapeutics which avoid the hazards of impure preparations is of great pharmaceutical interest.

The prior art discloses various strategies for the purification of factor IX, including the use of monoclonal antibody affinity technology to separate factor IX from other coagulation factors. However, it is important that such factor IX purifications include every effort to minimize the formation of factor $IX_a$ or degraded factor IX peptides. Since factor IX (the proenzyme) and activated factor IX ($IX_a$) are similar in structure, it is difficult to separate the two forms of factor IX by any purification strategy. Even antibody affinity technology is unlikely to achieve a separation since both molecules have most of their potential determinants in common, and the factor $IX_a$ contaminant (and potentially factor IX degradation peptides) would tend to be carried forward into the final product. It is believed that there is no presently known antibody of adequate differential sensitivity.

The present invention is related to improved means for preventing proteolytic conversion of factor IX to factor $IX_a$ or to degraded factor IX peptides as factor IX is purified, and for arresting proteolytic action on purified factor IX during storage thereof.

REPORTED DEVELOPMENTS

The purification of factor IX requires that it be separated from numerous other blood plasma proteins and other plasma macromolecules. Typically factor IX is produced from cryoprecipitate-free plasma. This plasma fraction is produced by rapidly freezing whole plasma, allowing it to thaw slowly and collecting the separated supernatant. See Pool, J. G., et al. *Nature*, 203, 312 (1964). Many proteins, including factor VIII, precipitate out of the slowly thawing plasma and can be removed by centrifugation.

In the practice of the prior art, the factor IX-containing cryoprecipitate-free supernatant plasma is typically mixed with an anion exchange resin or gel such as DEAE Sephadex®, DEAE cellulose, or DEAE Sepharose®, (in batch or column form) or alternately Al(OH)$_3$ gel, leading to adsorption of the factor IX along with other clotting factors with similar binding properties, and also adsorption of lesser amounts of other contaminating proteins. Initial fractionation with anion exchange resin particles takes advantage of the fact that certain clotting factors (such as factors II, VII, IX and X) are selectively adsorbed onto such resins owing to their negatively charged gamma carboxyglutamate residues. These proteins are also referred to as "vitamin K-dependent clotting factors" since a posttranslational vitamin K cofactor-dependent process attaches the gamma carboxy groups, such groups being necessary for proper binding of the coagulation factors to $Ca^{+2}$, lipid surfaces and platelets.

Typically, the bound factor IX is washed, and then eluted from the anion exchange resin using a buffered salt solution of high molarity. Inasmuch as such high molarity salt solution is considered osmotically incompatible with human tissues, practitioners of the prior art invariably subject their factor IX extracts to dialysis and filtration (or alternately ultrafiltration and diafiltration) which place the factor IX extract in concentrated form, but replace the high molarity salt solution with a physiologically-compatible low molarity salt solution.

The factor IX-enriched resin eluate (contaminated with significant amounts of other proteins, including clotting factors II, VII and X) is known as a prothrombin complex concentrate. Factor II (prothrombin) and the other vitamin K-dependent coagulation factors are known as "prothrombin complex" because of the above-mentioned similar binding properties. Hemophilia B patients have been typically treated with such concentrates.

In the practice of the prior art, the above-mentioned anion exchange chromatography may also be preceded or replaced by other steps. For example, cryoprecipitate-free plasma, to which citrate has been added, can be treated with barium chloride causing precipitation of barium citrate on which factor IX and certain other coagulation factors are bound. The proteins are isolated from the precipitate and then subjected to anion exchange chromatography. See, for example, Miletich, J. P. et al., *J. Biol. Chem.*, 253(19), 6908–6916 (1978). Factor IX may also be adsorbed to a gel of Al(OH)$_3$.

Alternatively, a second ion exchange resin step can be added. As disclosed in U.S. Pat. No. 4,447,416 (hereinafter the '416 patent), after anion exchange chromatography, the factor IX fraction is subjected to ultrafiltration and diafiltration against 0.15 Molar NaCl buffered with 20 mM citrate, pH6, and then subjected to a second phase of ion exchange chromatography using a sulfated dextran resin. Factor IX is eluted from this second resin when the salt concentration reaches 0.8 Molar. The factor IX, contained within a solution of high salt molarity, is then again subjected to ultrafiltration and diafiltration against physiologically acceptable 0.11 Molar NaCl, 20 mM citrate, pH 6.8, and then stored in lyophilized form. The method reported, however, leads to a factor IX product in which less than 10% of the protein is factor IX, more than 90% of the material consisting of contaminating protein species. No assays of factor $IX_a$ are reported in the '416 patent and no experiments are disclosed which would determine whether contaminating proteases will continue to generate factor $IX_a$, or degraded forms of factor IX, if the product were to be stored in other than lyophilized form.

Menache, D. et al., in *Blood*, 64(6), 1220–1227 (1984), using technology reflecting the '416 patent disclose a factor IX preparation, stated to be free of activated factor $IX_a$ and having a specific activity of approximately 5 units factor IX activity per mg total protein. Since the specific activity of pure factor IX is approximately 200 units/mg protein, the final product is considered to be heavily contaminated with other proteins, and because of the potential for protease activity, its long term non-thrombogenic status is doubtful.

Michalski et. al., *Vox Sang*, 55, 202–210 (1988) discloses a factor IX purifying strategy in which standard anion exchange chromatography of the prior art is followed by chromatography on a resin coated with heparin, a negatively charged mucopolysaccharide. The product is stated to be free of factor $IX_a$, as measured by an antithrombin III neutralization assay, but contains only 5% by weight of factor IX, the remainder being protein contaminants. It is clinically undesirable to administer such impure preparations owing to the potential for eventual activation of factor IX by one of the contaminating proteins present therein. Without evaluation of such concentrate in animal models sensitive to thrombogenic components as described in this application, the absence of thrombogenic risk is not verified.

Since blood plasma contains many proteins which have similar physical properties and which are very difficult to separate from factor IX, and because most purification procedures result in considerable proteolytic activation and/or degradation of factor IX, practitioners have tried to develop new strategies to obtain factor IX therapeutics having high specific activity (high purity) and being free of other protein contaminants.

Considerable emphasis has been placed on cloning the human factor IX gene in order to produce factor IX preparations which are free of other clotting factors and blood plasma proteases which tend to degrade Factor IX. Unfortunately to date, it has not been possible to isolate factor IX from such preparations in adequately pure form. In addition the obstacle of duplicating, in the genetically engineered product, the specific in vivo post translational modification of particular glutamic acid residues to yield the critical gamma-carboxyglutamic acid residues of factor IX has not been solved.

Antibodies specific to individual proteins have been a valuable tool in attempting to isolate coagulation factors in pure form. Following the technique of Koehler, G. and Milstein, C. (*Nature*, 256, 495–497 (1975)), Goodall, A. H. et al. identified monoclonal antibodies to factor IX and used them in preparative immunoaffinity chromatography to create a high specific activity factor IX. *Blood*, 59 (3), 664–670, (1982). However, the Goodall procedure does not solve the crucial clinical difficulty that factor $IX_a$ exists in native plasma and will be further produced by proteolytic activity during the preliminary steps of the protocol (conventional chromatography such as anion exchange) prior to immunoaffinity chromatography. No assays for factor $IX_a$ or degraded factor IX peptides were reported. No strategy for controlling thrombogenicity prior to immunoaffinity chromatography was disclosed, nor were test results in animal models sensitive to thrombogenic components reported.

Monoclonal antibody affinity techniques are very effective at separating factor IX from other clotting factors and have become the preferred purifying method of many researchers. However, in the present state of the art, factor IX obtained by immunoaffinity chromatography is consistently contaminated with copurifying factor $IX_a$, and/or other clinically unacceptable degraded forms of factor IX, which cross react with factor IX antibodies.

U.S. Pat. No. 4,786,726 (hereinafter the '726 patent) discloses a particular monoclonal antibody therein designated as "A-7". The development consists of recognizing that the binding of this antibody to factor IX is $Ca^{+2}$ dependent, and can be prevented by the addition of ethylene diaminetetracetic acid (EDTA). This provides a useful method of controlling elution of factor IX from the stationary phase of an affinity column following washing to remove protein contaminants. Factor IX is finally eluted from the antibody-resin complexes using calcium chelation. The development does not, however, improve the quality of the prothrombin complex concentrate applied to the immunoaffinity column, nor does it provide a way to separate factor IX from factor $IX_a$. No recognition is given of the necessity or means of controlling factor IX activation or degradation in early processing stages.

Smith, K. J. et al., *Thrombosis Research*, 33, 211–224 (1984), in a publication reflecting the '726 patent, failed in attempting to create an antibody which would recognize factor IX and not factor $IX_a$ (or vice-versa). The current art discloses no such antibody (which, in fact, because of structural considerations is likely to be very difficult to isolate) emphasizing the need for other purifying steps and methods which will solve the problem of activation of factor IX to factor $IX_a$, or its degradation to other clinically unsafe peptides.

In order to produce the most clinically acceptable factor IX, free of thrombogenic components, it is necessary to control decomposition of, or activation of, factor IX throughout the preparative procedure and especially in early stages thereof. Lack of a solution to this problem is consistently noted by the prior art. For example, it has been reported that immunoaffinity purified factor IX product showed contamination by lower molecular weight components (including $IX_a$) attributed to factor IX decomposition in the starting material.

In addition, in reference to another immunoaffinity purification system, H. A. Liebman et al. also notes the same inability to differentiate and separate factors IX and $IX_a$. *Blood*, 62(5), supp. 1, 288a (1983). See also Liebman, H. A. et al., *Proc. Natl. Acad. Sci. USA*, 82, 3879–3883, (1985).

The immunopurification system of H. Bessos et al. is reported to have generated a factor IX of high specific activity whose activity rapidly decayed after purification when the product was placed in a low ionic strength storage solution. *Thrombosis and Haemostasis*, 56(1), 86–89 (1986). This decay may have been caused by protease activity.

The prior art has also attempted, with only partial success, to prevent activation of factor IX to factor $IX_a$ using particular protease inhibitors many of which are organic compounds typically of high toxicity. These compounds are suitable for in vitro research application only and are very undesirable as reagents in protocols for clinical products. For example, the '726 patent specifies that immunoaffinity chromatography of factor IX must take place in the presence of benzamidine. To obtain factor IX sufficiently pure and stable for the creation of specific monoclonal antibodies, Goodall, A. H. et al. (*Blood* 59 (3) 664–670 (1982)) teaches the addition of the toxic organics benzamidine and diisopropylfluoro-phosphonate to factor IX-containing solutions.

The present invention relates to stabilizing factor IX against activation or degradation.

SUMMARY OF THE INVENTION

In accordance with the present invention, there is provided, in a process for purifying and preserving factor IX derived from human blood plasma or other source, the improvement of stabilizing factor IX in solution against activation to factor $IX_a$ or against degradation to peptides of altered length and/or conformation by adding one or more soluble organic or inorganic salts to the factor IX-containing solution to a concentration sufficient to prevent or substantially minimize activation of or degradation of factor IX but at a concentration insufficient to cause precipitation of, irreversible alterations in, or denaturation of the factor IX molecule, and maintaining the salt(s) in the solution at said concentration during storage or further treatment.

In one respect, the present invention involves protecting factor IX from activation to factor $IX_a$ or degradation to peptides of altered length and/or conformation during multi-step purification by minimizing the amount of time impure factor IX is present in solutions containing an insufficient concentration of salt. The improved processes of the invention are found to be particularly useful in preventing catalytic action by proteases upon factor IX. Accordingly, there is provided in a method of purifying factor IX in solution involving two or more sequential separation processes, the improvement which comprises adding, during or after a particular separation process, one or more soluble organic or inorganic salts to the solution containing factor IX to a concentration of salt sufficient to prevent or substantially minimize catalytic action by proteases upon factor IX, but at a total concentration of said salt or salts insufficient to cause precipitation of, irreversible alterations in, or denaturation of the factor IX molecule, and maintaining the partially purified protein in contact with said salt solution at said sufficient salt concentration for a period at least until the next separation process is commenced.

As will be described in detail below, a wide variety of water soluble organic and inorganic salts can be used in the practice of the invention. Preferred salts are water soluble alkali metal or alkaline earth metal salts, most preferably magnesium, potassium, sodium and lithium chloride or sodium sulfate. It is expected that the most widely used concentration of salt will fall within the range of about 0.4 to about 1.4 Molar.

Another aspect of the invention comprises an aqueous solution of partially purified factor IX having a predetermined specific activity and one or more water soluble organic or inorganic salts in a concentration sufficient to prevent or substantially minimize catalytic action by proteases upon factor IX, but insufficient to cause irreversible alterations in, precipitation of, or denaturation of the factor IX molecule, the solution when stored for at least about 12 hours at or below a temperature of 4° C., having also a factor IX activity of about 80 to about 100% of the predetermined activity.

A further aspect of the invention relates to the provision of a factor IX composition which is in therapeutic form and is stable in that it is capable of being stored as an aqueous solution without deteriorating for prolonged periods of time, for example, at least about 2 weeks at room temperature. Accordingly, the invention encompasses also a therapeutic composition comprising an aqueous solution of factor IX having a specific activity of greater than about 50 units factor IX activity/mg protein, and wherein the composition is capable of being stored for a period of time of about 2 weeks at a storage temperature up to 15–30° C., while remaining free of factor $IX_a$, degraded forms of factor IX and/or active forms of other clotting factors in concentrations which would tend to cause detectable adverse clinical effects in a human when said composition is administered in a therapeutic dose.

A further aspect of the invention provides a method of treating Christmas disease in a patient comprising administering to such patient an effective amount of one or more of the therapeutic compositions of this invention. As will be seen from the discussion below, a variety of inorganic and organic salts which are non-toxic to humans can be used in formulating such compositions in accordance with the present invention.

Important advantages afforded by the invention include: 1) improving the purity, safety and stability of factor IX therapeutics; and 2) introducing flexibility and economy into commercial factor IX production schedules. Still another advantage afforded by the invention is that stable highly purified factor IX can be produced without use of therapeutically undesirable and highly toxic organic protease inhibitors. In addition, the nature of the invention is such that it is widely applicable to many types of processes which have been developed for producing factor IX preparations, including those of low, intermediate or high purity.

DETAILED DESCRIPTION OF THE INVENTION

Figure 1:
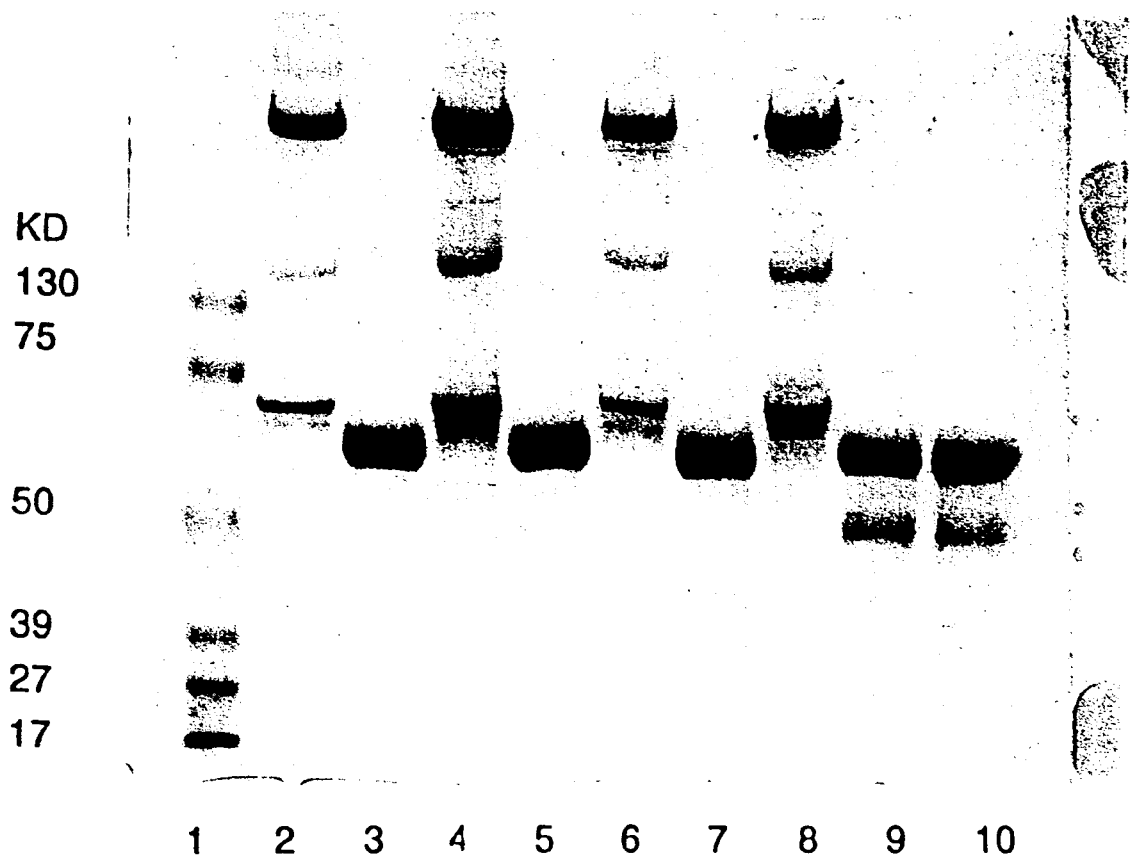
FIG. 1 is an SDS-polyacrylamide slab gel showing DEAE concentrates and final factor IX products produced therefrom by a typical prior art process or by a process of the present invention.

The present invention is based upon the recognition that water-soluble organic and inorganic salts can be used to protect factor IX from proteolysis, including activation to factor $IX_a$, during purification of factor IX. One of the important advantages of the present invention is that it can be used effectively in any number of different processes which are available for purifying factor IX. There follows a description of a basic type of process for producing purified concentrated factor IX.

The production of factor IX for therapeutic use in the treatment of hemophilia B (Christmas disease) traditionally begins with blood plasma which is subjected to freezing. This frozen plasma is then slowly thawed at which point clotting factor VIII and certain other proteins can be recovered as a cryoprecipitate. Factor IX and other proteins move into the soluble supernatant phase.

This factor IX-containing plasma fraction is then typically subjected to adsorption on an anion exchange resin. After washing the resin part.cles extensively with a dilute salt solution to remove unbound or weakly binding proteins, a high molarity salt solution is usually used to elute factor IX which is collected in a fraction known as the "prothrombin complex concentrate" because it also contains significant amounts of the other vitamin K-dependent or "prothrombin complex" clotting factors (factors II, VII and X, and also activated forms thereof).

Typically, this factor IX-enriched fraction is then subjected to a lengthy filter concentration and dialysis procedure which can take up to 24 hours for the purpose of replacing the high salt medium with a low salt molarity, physiologically compatible buffer. In earlier times, this form of the product was used for therapeutic purposes.

Typically, this low-salt form of prothrombin complex concentrate contained proteases which prematurely activate factor IX to clinically dangerous factor $IX_a$. Under these circumstances, factor IX is also degraded to other peptides which may also be clinically dangerous. Such proteolysis of factor IX is particularly severe when the factor IX is stored for prolonged periods in salt solutions of low molarity. Deaths have been reported from the administration of this type of product. Plat, P. M. et al., *Annals of Internal Medicine*, 81, 766–770 (1974).

In an attempt to improve on the clinically inadequate purity of prothrombin complex concentrate, researchers have modified the basic process described above, for example, by adding various additional steps or separation procedures, or by adopting alternate strategies to prevent proteolysis of factor IX and to remove additional contaminants. More recent protocols are typically a variation on the following: 1) cryoprecipitation; 2) anion exchange which takes advantage of the common specific adsorbability of vitamin K-dependent clotting factors; and 3) an additional separation procedure which separates factor IX from the other prothrombin complex proteins.

Examples of such additional separation procedures include the use of chromatography on an agarose gel to which heparin groups have been attached, cation exchange on a sulfated dextran gel, or immunoaffinity chromatography in which the stationary phase of the separation (purification) system consists of factor IX-specific antibodies.

Another strategy involves use of ammonium sulfate fractionation and/or elution of factor IX from an adsorption complex formed from precipitated barium salts followed by anion exchange chromatography. Selective adsorption to a gel of aluminum hydroxide has also been utilized. Still another strategy involves the use of an additional anion exchange resin which effects separation of prothrombin complex proteins which were not separated when previously contacted with different type anion exchange resin.

Still another approach is to apply whole plasma or cryoprecipitate-free plasma directly to a factor IX-specific immunoaffinity chromatography resin present in batch or column form.

Available methods for purifying factor IX, such as those described above, involve separation processes and manipulations. The term "separation process," as used herein, refers to a step which involves separating factor IX from one or more other peptides (proteins) in admixture therewith. The term "manipulation," as used herein, refers to a step which does not effect separation of factor IX from other peptides (proteins), but which is practiced before or after a separation process. Examples of manipulations are dialysis, sterile filtration, heat sterilization to inactivate contaminating microorganisms or virus particles in factor IX solutions, and also diafiltration wherein factor IX is selectively retained against a selectively permeable membrane while the solvent in which the factor IX is suspended is filtered through and replaced.

When a separation process or a manipulation of the prior art requires use of a salt, it is routinely performed using a low molarity salt solution (generally 0.15 M), except when the nature of the process or the manipulation requires that it be performed with the use of a high salt concentration. In the latter case, it is conventional to lower the salt concentration promptly after the step involving its use is completed and without eaffecting storage of factor IX therein. Examples of manipulations wherein a high salt concentration not intended to protect factor IX from proteolysis is removed promptly after the step involving its use include (1) eluting factor IX from a chromatography column using a high salt buffer and then removing the salt by procedures such as dialysis or by freezing and lyophilizing the eluate, thereby removing the salt by volatilization, or (2) heating a factor IX-containing solution to inactivate microorganisms or viruses. In the course of the development of this invention, it has been recognized that reducing the concentration of organic or inorganic salt in a factor IX-containing solution during or following completion of a separation or manipulation procedure provides a major opportunity for activation of factor IX to factor $IX_a$ or for degradation of factor IX to other factor IX-derived peptides. It is believed that there are two general reasons that the significance of proteolysis of factor IX and resultant production of factor $IX_a$ in low salt environments has gone unrecognized in the art.

First, high molarity salt solutions interfere with certain types of separation processes. For example, high concentrations of salts would prevent binding by factor IX to certain ion exchange resins or immunoaffinity columns. No separation could be effected.

Second, factor IX-containing high molarity salt solutions cannot be injected into patients because they are osmotically incompatible with living tissue. As a result, the prior art regards "excess" salt as something which should be removed from a factor IX preparation at the earliest convenience.

The use of salts at relatively high concentrations in accordance with the present invention enables factor IX to be protected not only during manipulations between or after separation processes, but during the separation processes themselves. The use of the "high" salt concentration in accordance with the present invention can be employed, as appropriate, in the various steps utilized in the purifying process up to and including that stage of the purification at which there have been removed from the Factor IX-containing solution those impurities which tend to activate Factor IX to Factor $IX_a$ and/or to degrade Factor IX to peptides of altered length and/or conformation. If desired, the high salt concentration can then be reduced. In the preferred embodiment of the present invention, the high salt concentration (for example, about 1 Molar or more) can be reduced somewhat (for example, to about 0.4 to about 0.6 Molar) just prior to the purifying step which involves immunoaffinity chromatography using monoclonal antibodies which effect separation of Factor IX from other coagulation factors and other proteins. Thereafter, the Factor IX can be eluted from the monoclonal antibodies and recovered in dilute form, for example, in a dilute solution having a Molarity below about 0.4.

The following publications disclose examples of factor IX purifications which can be modified in accordance with the present invention for the purpose of producing a therapeutic material of higher purity, ard improved safety and stability. In one exemplary embodiment of such modifications, there is included and maintained in the impure factor IX solution a soluble salt (for example, potassium chloride) in a relatively high concentration, for example, at least about 0.5 Molar.

(A) U.S. Pat. No. 4,447,416 discloses a process for purifying factor IX utilizing an anion exchange resin in a low molarity salt solution with the steps of clarification and concentration by filtering at low salt concentration following. After further purification on a sulfated dextran cation exchange resin, the solution is dialyzed against a low molarity salt solution.

(B) Michalski et al. *Vox. Sang.*, 55, 202–210 (1988) disclose a factor IX product purified by traditional anion exchange chromatography and the subsequent use of a heparin-linked resin. Numerous low ionic strength procedures are involved such as elution from the anion exchange resin with NaCl buffer, dilution prior to binding to the heparin-coated resin, and elution therefrom.

(C) Miletich J. P. et al. in *Methods in Enzymolocry*, 80, 221–228 (1981) disclose a factor IX product derived from successive steps of barium citrate adsorption, ammonium sulfate fractionation, ion exchange and dextran sulfate chromatography (and elutions therefrom) which place intermediate purity factor IX fractions for extensive periods of time in solutions having low concentrations of salts. No factor $IX_a$ assays or evaluations of thrombogenicity are reported.

(D) Bajaj, S. P., et al. *Preparative Biochemistry* 11(4) 397–412 (1981) report a factor IX preparation derived from a technique involving four sequential separation procedures involving the use of barium citrate adsorption and elution, ammonium sulfate fractionation, DEAE-Sephadex® chromatography, and heparin-agarose chromatography. Crude and intermediate purity factor IX are maintained in low molarity salt solutions for considerable periods during and between each separation procedure. No enzymatic assays for factor $IX_a$ or evaluations of thrombogenicity are reported.

(E) U.S. Pat. No. 4,786,726 discloses multi-step purification of factor IX involving the use of barium salt precipitation, anion exchange chromatography, ammonium sulfate precipitation, and dextran sulfate chromatography prior to further purification on an immunoaffinity column. The factor IX is manipulated with several extended periods of dialysis against factor IX-nonprotecting low molarity salt solutions.

(F) Goodall, A. H. et al. *Blood*, 59(3), 664–670 (1982), in a procedure representative of immunoaffinity methods, disclose the use of monoclonal antibodies to purify factor IX present in a prothrombin complex concentrate starting material, the concentrate having been prepared by standard methods, without regard to protecting the factor IX from activation or degradation in early stages.

Although monoclonal antibody columns have high specificity for factor IX and are effectively used to remove other contaminating coagulation factors, it is believed that there is not presently available an antibody affinity purification strategy which can bind factor IX and reject factor $IX_a$, (or vice-versa) (Smith, K. J. et al., *Thrombosis Research*, 33, 211–224, (1984)). In Tharakan, J. et al. *Vox. Sang.*, 58, 21–29 (1990), there is disclosed a high specific activity immunoaffinity purified factor IX product which is nonetheless contaminated by factor IX degradation products derived from traditionally prepared prothrombin complex starting material.

Expression of human clotting factor IX from recombinant DNA clones has been previously demonstrated in mammalian cells. Anson, D. S. et al., *Nature*, 315, 683–685 (1985), Jallat, S. et al., *EMBO Journal*, 9 (10), 3295–3301 (1990). Purification of such factor IX generally involves collection of a cell extract and then subjecting the extract to one or more of the above mentioned separation procedures. Protection of factor IX during purification from endogenous cell proteases may be accomplished by maximizing the amount of time factor IX-containing fractions are maintained in contact with relatively high concentrations of one or more of the organic or inorganic salts in accordance with the present invention.

It should be understood that a particular separation process or manipulation used in factor IX purification may be adversely affected by use of a relatively high salt concentration, as taught herein. If such is the case, the use of the relatively high salt concentration should, of course, be avoided for that particular separation process or manipulation, with the understanding that such high salt concentration can be used effectively in other purifying or accompanying steps which are not affected adversely, and in storage of the partially purified factor IX solution. Thus, one aspect of the present invention can be described as the recognition that protease-induced damage to factor IX which may occur within solutions containing low concentrations of salts may be substantially decreased by redesigning the purifying procedure to maximize the amount of time crude and intermediate purity factor IX fractions are maintained in a relatively high salt environment utilizing one or more soluble salts of the present invention.

A wide variety of different types of salts can be used in the practice of the present invention. One potential mechanism of action is that effective salts function by modifying the energetics of catalysis of relevant proteases. The effective salt may function by destabilizing proteases, by stabilizing the structure of factor IX, by reversibly altering the structure of factor IX so that it does not present to any particular protease those structural features which are normally attacked, by increasing the activation energy necessary to position and/or cleave factor IX at a protease active site, or by any combination of the above. Since the specific nature of all of the blood plasma or other proteases which can cleave factor IX is unknown, it is difficult to identify the specific mechanisms by which each of the useful proteolysis inhibitors functions. It is postulated that the factor IX molecule is strongly resistant to significant irreversible alterations In its tertiary structure caused by soluble inorganic or organic salts.

It is noted that there are many other causes for the denaturation of proteins (with resultant loss of catalytic activity or decay of three dimensional structure) during separation or manipulation procedures or during storage in solution. Examples of processes known to denature, break or otherwise adversely affect proteins in solution include shearing, binding to the surface of a vessel such as a glass wall, foaming of a solution, and oxidation of cysteine residues by atmospheric oxygen. The salt solutions useful in the practice of this invention may be effective also in arresting these other potential causes of factor IX degradation.

There can be used in the practice of this invention any water soluble inorganic or water soluble organic salt which is capable of reducing protease-caused cleavage of coagulation factor IX at a salt concentration which does not irreversibly alter the factor IX structure or cause factor IX to precipitate. The salts comprise a positively charged cationic component and a negatively charged anionic component which in aqueous media are dissociated to ionic form. The term "organic salt" refers to a salt in which either the cationic or anionic component thereof is a carbon-containing substance.

Examples of water soluble inorganic and organic salts for use as inhibitors of proteases which activate or degrade factor IX are: ammonium, alkali metal or alkaline earth metal halides; ammonium, alkali metal or alkaline earth metal thiocyanates; ammonium or alkali metal phosphates or sulfates; magnesium sulfate or phosphate; acetates of the alkaline earth or alkali metals; alkylammonium halides, including quaternary ammonium halides; and chlorides of imidazole, lysine and trihydroxyaminomethylmethane ("Tris").

Preferred salts for use in the practice of the present invention are sodium chloride; sodium and potassium thiocyanates; magnesium, potassium, and lithium chlorides; and sodium sulfate, with the most preferred salts being sodium chloride and sodium sulfate.

Effective concentrations of salts for use in the practice of the present invention can vary depending on the particular salt used. The lower limit of concentration is governed by how much of the salt is needed to inhibit factor IX degradation and activation. The upper limit is governed by that amount which can adversely affect factor IX and/or at which proportional benefits are not realized as the amount of salt is increased. Once the principle of protecting the factor IX molecule from degradation or proteolysis is recognized as taught herein, determination of optimal salt concentrations are readily obtained by simple incubation experiments as taught herein.

It should be appreciated also that there are factors which affect the range of concentrations over which a particular salt is effective. Such factors include the length of time or temperature for which protective effects are desired, the concentration of macromolecules, including proteases, present in the sample, and the nature of the manipulation, separation process and/or storage conditions under which protection is sought. These factors, coupled with the inherent ability of the particular salt to alter the energetics of proteolysis, should be taken into account respecting choice of effective concentrations.

It is believed that, for most applications, depending on the particular salt used, it will be satisfactory to use a salt concentration of about 0.4 to about 1.4 Molar.

It should be understood that a higher salt concentration can be used. Salts such as, for example, magnesium, potassium and lithium chloride and sodium sulfate are effective at the lower end of the amount range. These salts are particularly useful because factor IX-protecting effects can be realized at salt concentrations which are less likely to interfere with separation procedures such as those which involve the loading and binding of factor IX to an affinity column or ion exchange resin. Factor IX can therefore be protected continuously throughout a multistep purification procedure. There are other salts which will need to be used at the higher end of the range, for example, a concentration of at least about 0.7 Molar. A preferred amount range for the aforementioned preferred and most preferred salts is about 0.35 to about 3 Molar, dependent on the particular salt used.

As to relative effectiveness of various types of salts, in one series of tests 1 Molar concentrations of organic salts such as the hydrochlorides of Tris, lysine and imidazole, and sodium acetate were found to exhibit factor IX-stabilizing effects lower than those of a 1 M concentration of NaCl. Such organic salt solutions are protective, however, when compared to 0.15 M NaCl.

An important aspect of this invention is that a high salt-containing intermediate purity fraction of factor IX, which has been partially purified by ion exchange chromatography or another separation process, but not yet subject to immunoaffinity chromatography or other separation process, may be stored effectively for prolonged periods of time, for example, at least about 12 hours at 4° C. or at least about 3 months when stored frozen. In such storage, degradation or activation of factor IX is inhibited by virtue of the use with the factor IX of a relatively high concentration of salt as disclosed herein. This serves as a clinically important alternative to storing such fractions in the presence of toxic organic protease inhibitors which may be very difficult to remove from the final product. There are numerous processing advantages associated with being able to store intermediate purity fractions of factor IX during its purification.

Even factor IX products of the highest purity may contain traces of numerous proteases which will eventually degrade or activate factor IX, especially if the product, even at low temperature, is subject to long term storage in liquid form. In accordance with this invention and as an alternative to lyophilization or freezing, salts may be added to purified factor IX products to make long term storage in liquid form possible. For the purpose of providing a therapeutic form of the factor IX composition, the concentration of the salt in the composition should be reduced to a clinically acceptable level, for example, to about 0.15 M or lower. This can be accomplished by procedures such as dialysis, or by diafiltration prior to distributing the product to a clinical facility or a patient.

The purified, therapeutic form of factor IX preparations which result from the practice of the invention are expected not to trigger unwanted clinical consequences (such as myocardial infarction, thrombosis, and disseminated intravascular coagulation) which may otherwise result from administration of currently available factor IX products. The example section below provides data which validate the increased safety of factor IX prepared according to the process of the present invention.

There follows a description of a preferred overall factor IX purification for use in the practice of the present invention.

The preferred purification utilizes cryoprecipitation of blood plasma to remove proteins such as factor VIII, followed by anion exchange chromatography which takes advantage of the specific adsorbability of vitamin K-dependent clotting factors, followed by immunoaffinity chromatography using monoclonal antibodies, the last mentioned separation process having great specificity for factor IX compared with other protein species.

The preferred anion exchange resin for purifying factor IX is a highly hydrophilic bead formed gel of epichlorohydrin-crosslinked dextran to which diethylaminoethyl ether (DEAE) exchange groups are attached such as DEAE-Sephadex$^R$ A-50 available from Pharmacia, Uppsala, Sweden. The temperature is maintained below 15° C., and preferably below 4° C., during the Sephadex adsorption equilibration process. Although factor IX is bound to DEAE-Sephadex$^R$ A-50 more quickly and completely at 20° C. than at 4° C., it is recommended that the temperature be as low as possible to minimize protease activity on factor IX. Accordingly, adsorption of factor IX at 4° C. is preferred. Factor $IX_a$ is also minimized as a contaminant in the final product by maintaining factor IX fractions (until such time as they have been separated from remaining contaminating proteases on a monoclonal antibody column) in a low temperature environment (such as 4° C. or below) in the relatively high molarity salt solutions of the present invention.

According to the preferred practice of this invention, proteolysis of factor IX is deterred in the anion exchange chromatography eluates by maintaining the protein in the presence of one or more suitable organic or inorganic salts at relatively high molarity (for example, about 1 Molar or more) until immediately prior to subjecting the factor IX enriched fractions to the further separation procedure of immunoaffinity chromatography using monoclonal antibodies which are used to separate factor IX from remaining coagulation factors and other proteins. In preferred form, prior to treatment with monoclonal antibodies, the molarity of the solution is reduced to some extent, for example, to about 0.5 M. The affinity of the monoclonal antibodies for factor IX separates it from remaining materials which would tend to activate factor IX to factor $IX_a$ and/or degrade factor IX to peptides of altered length and/or conformation. After separating factor IX from the monoclonal antibodies, it can be recovered, and even stored, in dilute form, if desired.

In connection with evaluating the purity of factor IX compositions that are capable of being produced by the present invention, two parameters, protein concentration and specific activity, must be determined.

Measurements which determine the protein concentrations in factor IX samples vary depending upon the precise method used. In the practice of this invention, the concentration of protein in factor IX samples is determined at 280 nm based on an extinction coefficient for a 10 mg/ml solution of pure factor IX of 13.7 units in a one centimeter pathway. Corrections for Rayleigh scattering are made following the methods of Bloom, J. W. et al., *Biochemistry*, 18, 4419–4425 (1979). See also Shapiro, S. S. et al., *Thromb. Diath. Haemorr.*, 16, 469 (1966).

Many assay methods have been reported in the art for evaluation of the specific activity (units factor IX activity/mg protein) of factor IX compositions. Such assay methods often fail to make corrections for contamination of the factor IX sample by factor $IX_a$. As a result, it is difficult to evaluate the purity and safety of factor IX therapeutics produced by different methods and/or assayed according to different protocols.

Some of the assays which are presently used include a two stage clotting assay, (Leibman, H. A. et al., *Proc. Natl. Acad. Sci.*, USA, 82, 3879–3883 (1985)); an assay based on the single stage activated partial thromboplastin time ("APTT"), Smith, K. J. et al., *Blood*, 72, 1269–1277 (1988); and assays which are modifications of the APTT test, for example, Jenny, R. et al., *Preparative Biochemistry*, 16, 227–245 (1986). Assays based on antigenic potency of factor IX have also been proposed as a measure of purity (Smith, K. J. et al., *Thromb. Haemostas.*, 58, 349 (1987)).

For the purpose of the present invention, the specific activity of factor IX compositions is assayed according to the single stage activated partial throinboplastin time "APTT" procedure of Smith, K. J. et al. *Blood*, 72, 1269–1277 (1988).

In prior art assays, many investigators have also used as a factor IX standard human plasma samples to which an assumed potency of 1.0 unit/ml is assigned. However, it must be emphasized that normal human plasma often contains a factor IX concentration significantly different from 1.0 unit/ml. For present purposes, reference is made to the International Reference Standard of factor IX, WHO #1, supplied by the World Health Organization.

Literature values for the specific activity of purified factor IX have been found to range from 130 to 220 units/mg. Differences in methods of protein determination, assay technique and calibration standards probably account for the reported differences. Compare Smith, K. J. et al., *Bloodp*, 72, 1269–1277 (1988) (134–155 units/mg); Bajaj, P. S. et al., *Preparative Biochemistry*, 11(4), 397–412 (1981) (180–220 units/mg); Osterud, B. et al., *J. Biol. Chem.*, 253(17), 5946–5951, (1978) (207 units/mg); Jenny, R. et al., *Preparative Biochemistry*, 16, 227–245 (1986) (132 units/mg).

Comparing results from different laboratory groups which utilize different methods to assay factor $IX_a$ is also very difficult. This is particularly important since factor IX and factor $IX_a$ can each interfere with assays designed to detect the other. An additional contribution associated with the development of this invention comprises the provision of a high sensitivity assay for factor $IX_a$ based on the partial thromboplastin test ("PTT"). The assay herein reported is not affected by the presence of factor IX, and as demonstrated in the example section below, validates the utility of the factor IX stabilizing processes of the present invention.

Therapeutic factor IX-containing compositions useful in the treatment of Christmas disease need not be comprised of factor IX at the absolute limit of specific activity as long as remaining protein contaminants will not cause detectable adverse clinical. effects in humans when such compositions are administered in otherwise therapeutic doses. As demonstrated in the example section below, the purification procedure of Example 1 can be used to produce factor IX for therapeutic use with a specific activity of at least 194 units/mg protein with a factor $IX_a$ contamination level of less than 0.02% (w/w). Factor IX compositions suitable for injection into a patient can be prepared, for example, by reconstitution with a pharmacologically acceptable diluent of a lyophilized sample comprising purified factor IX and stabilizing salts.

Among the techniques which can be used to show the purity of the resultant factor IX, and the minimization of contaminating factor $IX_a$ or factor IX degradation peptides in the therapeutic compositions of this invention, are sodium dodecylsulfate polyacrylamide gel electrophoresis (SDS-PAGE), Western blotting of electrophoresed factor IX-containing samples, and direct enzymatic assays for factor IX and factor $IX_a$.

In the practice of this invention, and because of difficulties in correlating in vitro assays with in vivo thrombogenic events, the potential thrombogenicity of purified factor IX preparations is evaluated using (1) the Wessler Rabbit Stasis Assay, (2) SDS-PAGE and Western blots to determine the amount of peptide(s) having an approximate molecular weight of 54 kDa, and (3) a new modified form of the APTT assay to determine the Level of factor IXa or of other peptides causing IXa-like activity. It is believed that the best currently available indicator of safety of therapeutic factor IX preparations is provided when the sample has a low response in the rabbit stasis test, contains (by SDS-PAGE) less than 10% of 54 kDa material, and gives further indication of having a low factor $IX_a$ content as measured in a modified (see Example 3 below) APTT test.

EXAMPLES

The following examples are illustrative of the practice of the invention.

Example 1
Purification Of Factor IX

This example demonstrates the purification of preparative quantities of therapeutically useful factor IX from blood plasma utilizing high concentrations of sodium chloride at particular steps to prevent proteolytic damage to factor IX.

A commercial manufacturing quantity of frozen plasma was allowed to thaw slowly at about 0° C. producing supernatant and precipitated fractions (see Pool, J. G. et al., *Nature*, 203, 312 (1964)). The supernatant fraction of the plasma which remains after cryoprecipitation contains factor IX and much of the original concentrations of factors II, VII and X. To the supernatant plasma fraction at about 4° C. were added DEAE-Sephadex$^R$ A-50 anion exchange beads (about 1.5 g/liter of supernatant). The resulting suspension was stirred gently for one hour in the cold as factor IX bound to the resin beads. Approximately 96% weight percent of the factor IX originally present in the plasma was localized on the resin beads. Other prothrombin complex proteins also bind. The resin beads with retained protein were collected by filtering and then washed with a volume of wash buffer,. precooled to about 4° C., which was at least equal to the volume of the cryoprecipitate-free supernatant. The wash buffer comprised a solution of 0.2 M NaCl, 0.01 M $Na_3$ citrate, pH 7.0, and 0.04 unit/ml sodium heparin. The ionic strength of the wash buffer was insufficient to cause significant dissociation of factor IX from Sephadex® beads. Eluting buffer (an aqueous solution of 2M NaCl with 10 mM sodium citrate, pH 7.0, and precooled to about 4° C.) was added and then gently stirred with the resin beads for 30 minutes. The resulting eluate was collected and held or processed further. Elution of the resin beads may be repeated and the eluates combined. Temperature control was maintained at between 2 and 8° C. for each of the steps of the DEAE-Sephadex® binding and elution procedure.

The elution of the factor IX-enriched fraction (prothrombin complex) from the DEAE-Sephadex$^R$ resin with a solution of 2M NaCl buffered with 10 mM sodium citrate, results in a combined eluate fraction whose final NaCl molarity (because of the lower ionic strength of the void volume solution) is approximately 1.0 Molar.

Once clarified and sterile filtered, the combined eluate (the "stable factor IX-enriched fraction" of this invention) was stored frozen at or below −40° C. prior to subsequent processing. Storage in the frozen state at or below −40° C. for 4 weeks or less does not affect the usefulness of the factor IX-containing samples. As a result of the stabilizing influence of the salts useful in the practice of the invention, storage for commercially practicable periods of time results in intermediate purity factor IX preparations having less than 10% loss of potency and showing little or no activation or degradation. This would not be the case if storage were effected in a buffer containing a lower molarity of salt, such as 0.15 M NaCl, even at −40° C.

Alternatively, the stable factor IX-enriched fraction was stored at 4° C. for up to 12 hours prior to being further processed. This procedure is. in contrast to prior art methods which teach that the eluate should be dialyzed or diafiltered extensively against a buffer of low salt concentration prior to further purification or clinical use.

Immediately prior to applying the "stable Factor IX enriched fraction" to a monoclonal antibody affinity column, it is diluted 1:1 with water reducing the sodium chloride concentration of the preparation to 0.5 Molar. The factor IX-containing prothrombin complex solution is loaded on a monoclonal antibody column, washed extensively and eluted with 3 M sodium thiocyanate. Testing of the eluate for degraded factor IX or for factor $IX_a$ shows them to be present at very low levels, allowing completion of the fractionation.

Preparation and utilization of monoclonal antibodies for immunoaffinity chromatography of the stable factor IX enriched fraction follow well established procedures. Purification of factor IX sufficiently pure for the production of monoclonal antibodies followed the procedure of Osterud, B. et al., *J. Biol. Chem.*, 253(17), 5946–5951 (1978). Spleens from mice previously injected with highly purified factor IX were removed and cells therefrom fused according to a standard procedure. Brown, J. P., et al., *J. Biol. Chem.*, 225, 4980–4983 (1980). Details of preparing and operating the immunoadsorbent system are as described in the specification "Immunoadsorbent, and Method of Recovering Vitamin-K Dependent Protein Therewith" EPO Serial No. 84-301162.8, published on Sep. 12, 1984 bearing number 0 118 256.

Factor IX was eluted from the monoclonal antibody column in a solution of 3 M sodium thiocyanate, 50 mM Tris.HCl, 10 mM EDTA, pH 8.0, and then diafiltered against 50 mM NaCl, 5 mM histidine, pH 7.0. The diafiltered factor IX solution was then subject to ultrafiltration against a YM100 membrane (Amicon Co. Danvers, Mass.) having a molecular weight cutoff for globular proteins of 100 kDa, thereby allowing factor IX to pass through the membrane with retention of viral particles. The factor IX-containing filtrate was collected, and then subject to filter concentration against a membrane suitable for retaining globular proteins with molecular weights greater than 10 kDa. The purified factor IX solution was then frozen and stored at −70° C. prior to final processing, thereby accommodating a commercial production schedule. The purified factor IX solution was finally subject to chromatography on a bead-formed agarose gel containing positively charged aminohexyl groups (AH Sepharose® 4B, Pharmacia, Uppsala, Sweden). The agarose gel chromatography accomplishes no actual further enhancement of purity of factor IX with respect to other coagulation factors, but serves to concentrate factor IX and remove trace levels of factor IX antibody which may have leaked from the monoclonal antibody column. Other commercially available gels can also be used.

After allowing factor IX to bind to the agarose gel beads, the gel was washed with 0.15 M NaCl, 10 mM histidine.HCL, 5 mM lysine.HCL, pH 7.0. Factor IX was eluted from the gel with a solution of 0.05 M $CaCl_2$, 0.15 M NaCl, 10 mM histidine.HCl, pH 7.0. The eluate was then diafiltered against 66 mM NaCl, 10 mM histidine.HCl, 3% (w/v) mannitol, pH 7.0, clarified, sterile filtered and stored at −40° C. or below. Alternatively the filtered solution may be freeze dried. The resulting material is the "improved factor IX final product" of the invention and has a specific activity which averages 180–200 units activity/mg protein.

Example 2

A Comparison with Prior Art Products

It is disclosed in the prior art that prothrombin complex concentrate, in approximately 1M–2M of NaCl, should be subject to lengthy manipulations such as dialysis, taking perhaps 24 hours, to reduce the salt concentration of the factor IX-containing isolate to the physiological range (about 0.15 Molar) for clinical use, or prior to further purification under low ionic strength conditions.

A comparison was made of the clarified, filtered prothrombin complex concentrate maintained in a 1.0 M NaCl solution containing also 10 mM sodium citrate, pH 7.0 ("the stable factor IX enriched fraction" of Example 1) with a prior art-type DEAE-Sephadex anion exchange chromatography eluate (a prothrombin complex concentrate) which was, according to standard practice, subject to dialysis or diafiltration to reduce its salt concentration to the physiological range. Both types of eluate fractions were then subject to further purification using monoclonal antibodies as described above resulting in an "improved factor IX final product", and a typical prior art final product.

Table 1 shows purity results for the final factor IX product of Example 1 and typical prior art process final product. As can be seen from the table, individual lots of "improved factor IX final product" derived from "stable factor IX-enriched fraction" show much less contamination by factor $IX_a$ than final product derived from DEAE Sephadex anion exchange eluates which, consistent with the prior art, were subject to diafiltration into isotonic buffer solution for 3–4 hours with subsequent frozen storage prior to being applied to an immunoaffinity column. Factor IX was assayed by the "APTT" method according to Smith, K. J. et al., Blood, 72, 1269–1277 (1988). Factor $IX_a$ was assayed by the partial thromboplastin test, "PTT", Varadi, K. et al., *Thromb. Haemos.*, 35, 576–585 (1976) as modified according to the protocol of Example 3 below. The decreased contamination with factor $IX_a$ in the improved product is further validated by the longer clotting times, in seconds, in the factor $IX_a$ assay as presented in Table 1.

TABLE 1

Comparative Assay Results of Factor IX Final Products

| | Factor IX units/ml | Factor $IX_a$ units/ml | Clotting Time in $IX_a$ assay, Sec. (1:10 Dilution) | $FIX_a$/FIX Ratio as % | FIX/$FIX_a$ Ratio |
|---|---|---|---|---|---|
| Prior Art Factor IX Final Product | | | | | |
| Lot 1 | 98.0 | 0.4875 | 63.1 | 0.4974 | 201 |
| Lot 2 | 100.0 | 0.4375 | 62.6 | 0.4375 | 229 |
| Lot 3 | 103.0 | 0.2350 | 64.0 | 0.2282 | 438 |
| Lot 4 | 102.0 | 0.3500 | 52.5 | 0.3431 | 291 |
| Lot 5 | 115.0 | 0.2625 | 68.0 | 0.2283 | 438 |
| Improved Process Factor IX Final Product | | | | | |
| Lot 6 | 78.0 | 0.0286 | 146.2 | 0.0376 | 2,727 |
| Lot 7 | 92.0 | 0.0278 | 151.1 | 0.0302 | 3,309 |
| Lot 8 | 125.0 | 0.0247 | 160.3 | 0.0198 | 5,060 |
| Lot 9 | 102.0 | 0.0088 | 225.0 | 0.0086 | 11,591 |
| Lot 10 | 110.0 | 0.0423 | 134.3 | 0.0385 | 2,600 |

Anion exchange chromatography eluates and final products derived therefrom, when analyzed using sodium dodecylsulfate polyacrylamide gel electrophoresis (SDS-PAGE) according to the procedure of Weber, K. et al., *J. Biol. Chem.*, 244, 4406–4412, (1969) or as modified by Laemli, U. K. *Nature*, 227, 680–685 (1970), using an acrylamide concentration gradient of 4 to 12%, demonstrate (see FIG. 1) that prior art-type anion exchange chromatography eluate (prothrombin complex) and resultant final product are heavily contaminated with a band of apparent molecular weight of 54,000, characteristic of factor $IX_a$, (and certain factor IX degradation peptides), whereas this contaminant is much less apparent in the gel lanes corresponding to the stable factor IX-enriched fraction of the invention and final product derived therefrom. The lanes of the slab gel (FIG. 1) are loaded with approximately 14 μg of protein in the case of DEAE concentrates and approximately 9 μg for final products derived therefrom. Lane 1 of the Figure shows appropriate molecular weight markers. Lanes 2, 4 and 6 show individual lots of stable factor IX-enriched fraction derived from DEAE-Sephadex® chromatography according to the procedure of Example 1. Lanes 3, 5 and 7 comprise samples of the respective final products derived therefrom. Lane 8 comprises a sample of DEAE concentrate prepared by a non-optimized prior art procedure which does not use high concentrations of salt to protect factor IX. Lanes 9 and 10 present duplicate samples of final product derived therefrom.

Figure 2:
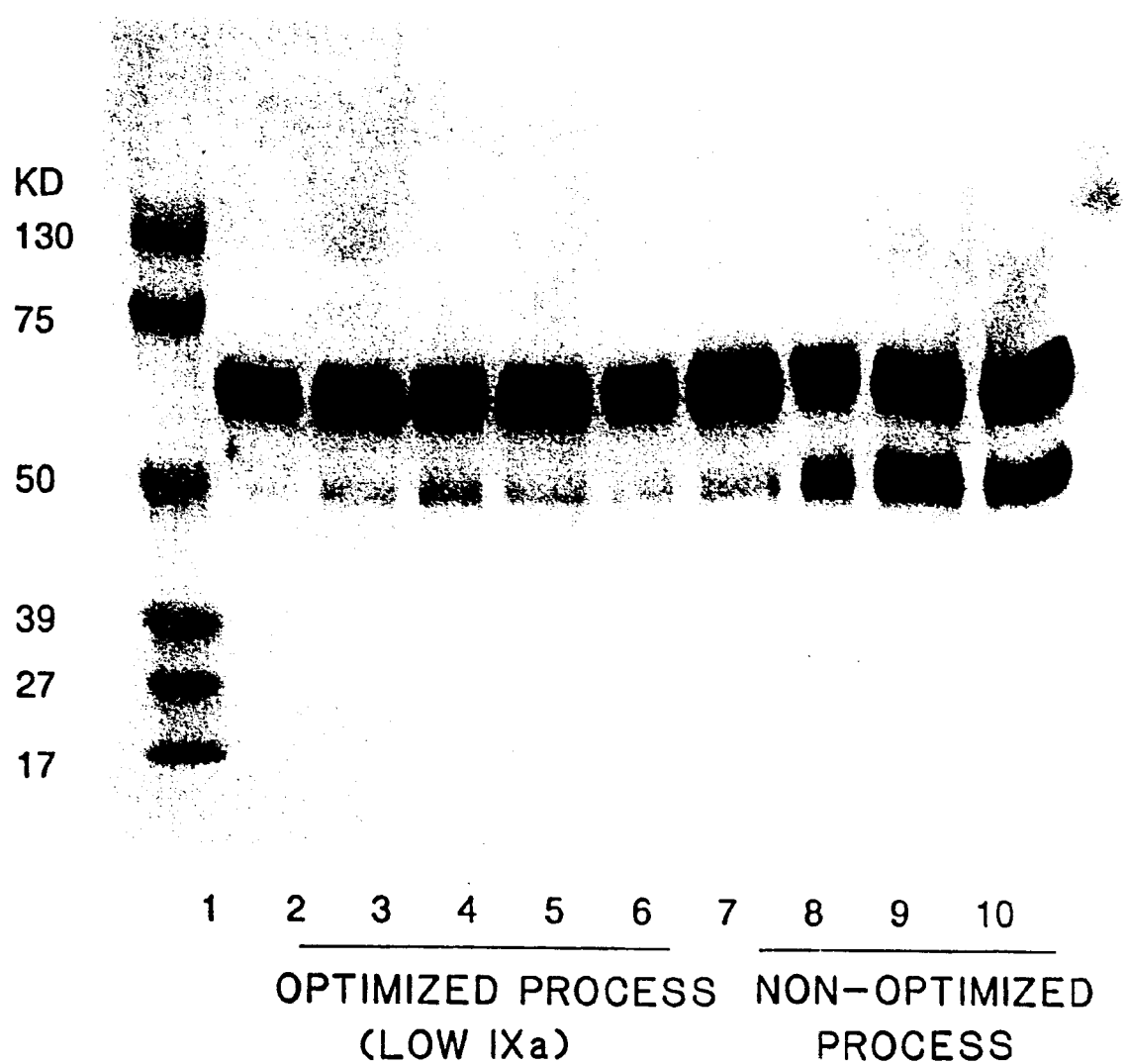
FIG. 2 is a Western blot showing DEAE concentrates and final factor IX products produced therefrom by a typical prior art process or by a process of the present invention.

Factor $IX_a$ contamination of the final factor IX products and anion exchange chromatography eluates (both produced via the improved process, and according to the prior art) was also compared using the highly sensitive Western blot technique. Factor $IX_a$ was detected by cross-reactivity of anti-factor IX antibody. In this procedure, the test samples were subjected to electrophoresis in a 4 to 12% acrylamide gradient gel in the presence of sodium dodecyl sulfate detergent. The proteins were then blotted and immobilized onto a nitrocellulose sheet. The pattern was visualized using rabbit anti-serum to human factor IX and horseradish peroxidase conjugate of goat anti-rabbit IgG. Color was finally developed using 4-chloro-1-naphthol and hydrogen peroxide. (See Pasternack et al., *Nature*, 322,740 (1986)). FIG. 2 demonstrates that the new process leads to a final product having only traces of factor $IX_a$ even when the gels are overloaded, as compared with the typical result of the prior art. The gel lanes in FIG. 2 correspond exactly to the gel lanes in FIG. 1 and represent the Western blot of a duplicate of the SDS-PAGE gel shown in FIG. 1. The gel lanes are loaded with approximately 14 μg for samples comprising DEAE concentrates and 0.07 μg for lanes containing final products.

Example 3

An Improved Assay for Factor $IX_a$ in Factor IX Preparations

In connection with the work on the present invention, an improved coagulation assay for factor $IX_a$, or for degraded 54 kDa factor IX-derived peptides or other proteins having factor $IX_a$-like activity, was developed and standardized to provide the art relating to blood purification with an improved analytical method. The principle of the new coagulant assay, which is highly sensitive, is based on the partial thromboplastin test ("PTT") and further demonstrates the lack of factor $IX_a$ activity in factor IX purified in accordance with the present invention. The assay is useful in predicting in vivo thrombogenicity of factor IX preparations, especially when used in conjunction with the in vivo assays of Example 7.

The potency of factor $IX_a$ or of peptides conferring factor $IX_a$-like activity is calculated directly based on clotting time in a one step assay. The phospholipid reagent used in the assay was derived from bovine brain and was used without activator. Thrombofax®, Ortho Diagnostic Systems, Raritan, N.J. Typical PTT procedure was modified by adding $BaSO_4$-adsorbed bovine plasma to factor IX-deficient human plasma in the assay protocol thereby increasing the supply of labile factors V and VIII.

This method is used for the measurement of activated factor $IX_a$ in factor IX final products, as well as for monitoring ili-process samples. The results from a spike test with factor IX samples showed good linearity and reproducibility for the factor $IX_a$ assay in the range of 0.0005 $IX_a$ units/ml to 0.05 $IX_a$ units/ml. Very small quantities of factor $IX_a$ in factor IX preparations can therefore be measured.

The effect of purified factor IX on the factor $IX_a$ assay was also studied by comparison of factor $IX_a$ spiked with factor IX dilutions and factor IX spiked with factor $IX_a$ dilutions. Factor IX does not interfere with the factor $IX_a$ assay. The assay is readily adapted to monitoring other factor IX preparative procedures. The factor $IX_a$ concentration data provided in Table 1 were calculated according to this procedure.

Only extremely low levels of factor $IX_a$ were found in the final monoclonal antibody-purified factor IX product produced according to the procedure of Example 1. Example 4 to 8 of the invention further demonstrate the purities and stabilities of factor IX which can be achieved by using various types of salt environments in accordance with the present invention.

Example 4

Stabilization of Factor IX at Different NaCl Concentrations

This example demonstrates the effects of different sodium chloride concentrations on the stability of factor IX in intermediate purity preparations (DEAE Sephadex® eluate fractions) over a 5-day period of storage at 4° C.

Prothrombin complex (containing factor IX, significant quantities of factors II, VII, X and numerous other contaminating proteins) is eluted from the DEAE-Sephadex® resin using 2M NaCl in accord with the procedure of Example 1. Both a first and a second eluate from the resin are collected and separately stored at 4° C. Eluted fractions achieve different final NaCl molarities (0.96–1.4 M) as the buffer present in the void volume of the resin must be displaced.

The samples of the eluates which were generated for this example are:

(A) from the 1st column elution at 0.956 M NaCl (B) a sample of material (A) diluted to 0.524 M NaCl (C) a sample of material (A) subject to ultrafiltration and diafiltration as in the typical prior art process, reducing the NaCl concentration to 0.056 M.

(D) a portion of sample (C) is on completion of the filtration procedure then brought back to 0.481 M of NaCl for analysis over 5 days.

(E) from the second column elution at 1.4 M of NaCl.

(F) a sample of material (E) diluted to 0.532M NaCl.

Once prepared, these samples were stored at 4° C. and then examined at zero, one, two and five days time for factor IX and for factor $IX_a$. Factor IX was assayed in a single stage activated partial thromboplastin time "APTT" procedure according to the method of Smith, K. J. et al. *Blood*, 72, 1269–1277 (1988), and factor IX, levels were determined using the new factor $IX_a$ assay presented in Example 3. Table 2 demonstrates that NaCl of 1.4 M or higher concentration results in maximal protection of factor IX against protease activity and minimizes production of factor $IX_a$ under the conditions indicated.

This example illustrates that the use of a relatively high concentration of salt in accordance with the present invention is effective over a wide temperature range.

A sample of DEAE Sephadex® eluate produced by the procedure of Example 1 above, which had been clarified and sterile filtered and containing 1M of NaCl and 10 mM sodium citrate, pH 7.0, was thawed after storage at −80° C. Separate five ml aliquots of the sample were dialyzed overnight at either 3° C. or 25° C., against 1.0, 0.75, 0.5, or 0.15 M sodium chloride solutions and then analyzed by Western blots and in factor IX and IXa activity assays. At low concentrations of dialysis salt, factor IX activation is substantial—even at 3° C. For example, when held at 3° C. and at 0.15 M of NaCl, approximately two thirds of the original factor IX is degraded after 12 hours. Factor $IX_a$ levels were also observed to drop in samples dialyzed at low salt concentration, at 3 or 25° C., providing further evidence of the potential extent of proteolysis of prothrombin concentrates.

Figure 3:
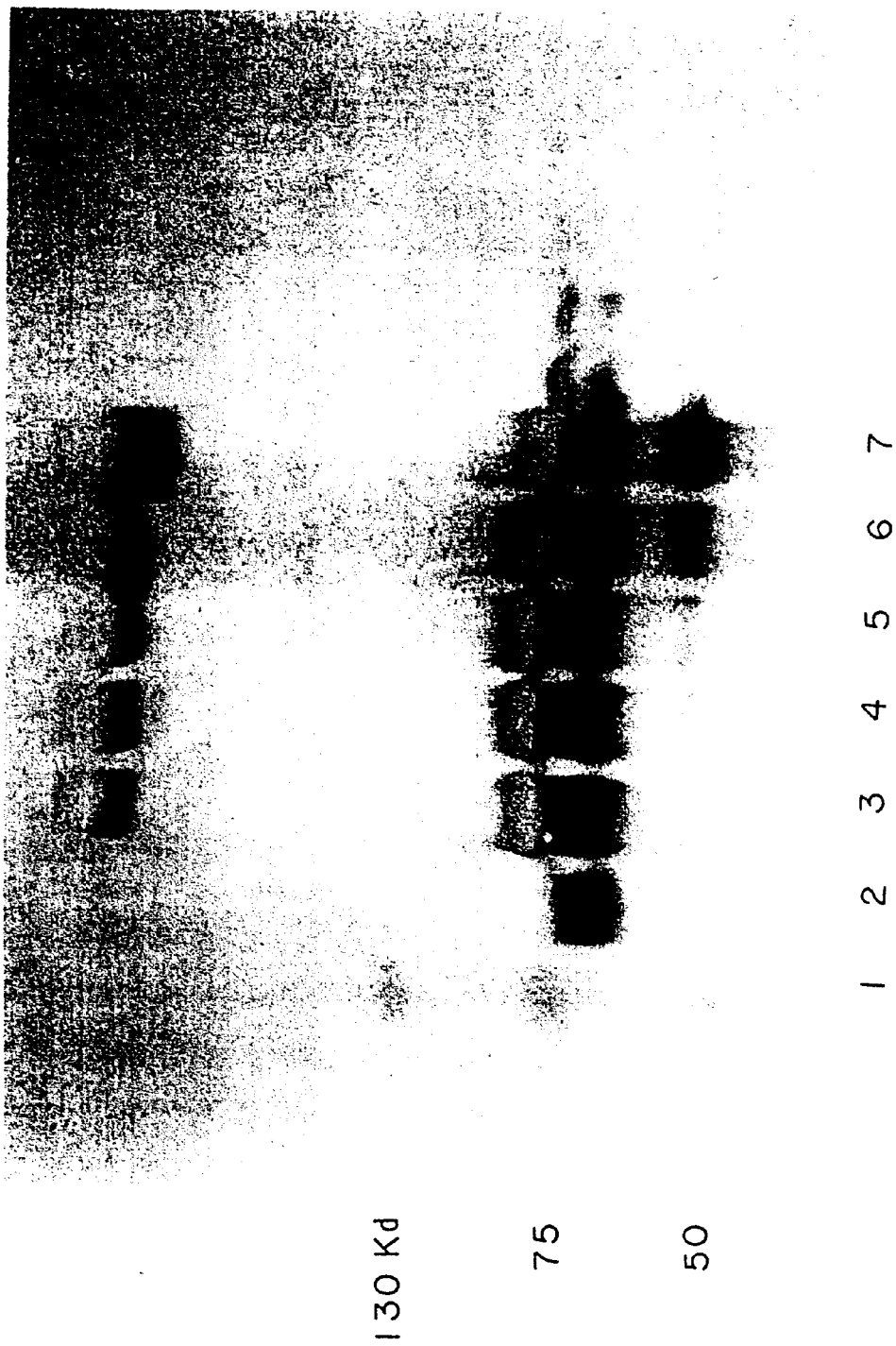
FIG. 3 is a Western blot showing the levels of proteolysis of factor IX which occur at 25° C. in samples of factor IX-containing DEAE concentrate dialyzed against different molarities of sodium chloride.

FIG. 3 presents the result of a Western blot at 25° C. Results at 3° C. were very similar. The respective lanes of the blot are (1) molecular weight markers; (2) a control consisting of frozen DEAE concentrate-eluate from DEAE-Sephadex® resin maintained in high salt according to the practice of this invention; (3) a thawed sample of DEAE concentrate (produced according to the procedure of Example 1 and containing also approximately 1M of NaCl) applied directly to the parent acrylamide gel without overnight dialysis; (4) a sample of DEAE concentrate produced according to the procedure of Example 1 and dialyzed overnight against 1.0 M NaCl; (5) a sample as in (4) above

TABLE 2

The Effect of Sodium Chloride Concentration on the Stability of DEAE-Sephadex Anion Exchange Chromatography Eluate preparations at 4° C.

|  | Final NaCl Molarity | F.IX (%) U/ML | $F.IX_a$ (%) U/ML | F.IX (%) U/ML | $F.IX_a$ (%) U/ML |
|---|---|---|---|---|---|
|  |  | 0 Days |  | 1 Day |  |
| Sample A | 0.956 | 16.5(100) | 0.0500(100) | 17.0(103) | 0.0500(100) |
| Sample B | 0.524 | 9.1(100) |  | 8.2(90) | 0.0385 |
| Sample C | 0.056 | 14.0(100) | 0.0125(100) | 9.5(68) | 0.0260(208) |
| Sample D | 0.481 | 11.0(100) |  | 8.6(78) | 0.0339 |
| Sample E | 1.40 | 4.1(100) | 0.0143(100) | 4.4(107) | 0.0159(100) |
| Sample F | 0.532 | 1.35(100) |  | 1.2(89) | 0.0079 |
|  |  | 2 Days |  | 5 Day |  |
| Sample A | 0.956 | 16.5(100) | 0.0408(82) | 19.8(118) | 0.0909(223) |
| Sample B | 0.524 | 6.2(68) | 0.0400 | 3.9(43) | 0.0667 |
| Sample C | 0.056 | 6.5(46) | 0.0297(238) | 2.5(19) | 0.3226(2581) |
| Sample D | 0.481 | 6.2(56) | 0.0238 | 2.7(25) | 0.0385 |
| Sample E | 1.40 | 3.8(86) | 0.0100(70) | 5.0(131) | 0.0294(294) |
| Sample F | 0.532 | 0.88(65) | 0.0044 | 0.32(24) | 0.0093 |

From Table 2, it can be seen that use of the present invention has a profound effect on the stability of factor IX in prothrombin complex fractions. The results for 0 and 5 day timepoints were also confirmed in the Western blot assay system of Example 2 using an anti-factor IX monoclonal antibody which also reacts with factor $IX_a$ and other 54 kDa factor IX-derived peptides.

Example 5

Effect Of Salt Concentration On Factor IX Stability at Two Different Temperatures but dialyzed against 0.75 M NaCl; (6) a sample as in (4) above but dialyzed against 0.5 M NaCl; and (7) a sample as in (4) above but dialyzed against 0.15 M NaCl.

Example 6

Use Of Different Salts

This example demonstrates that a variety of soluble salts exhibit factor IX-protective effects.

A sample of DEAE Sephadex® eluate produced according to the procedure of Example 1 and containing 1 M of NaCl and 10 mM sodium citrate, pH 7.0 was clarified and sterile filtered prior to storage at −80° C. Separate five ml aliquots of the thawed solution were dialyzed overnight at 3°

C. against 1 Molar solutions of sodium acetate, lithium chloride, magnesium chloride, potassium chloride, sodium chloride or sodium sulfate. The dialyzed solutions were assayed for factor IX, factor $IX_a$ and also analyzed in the non-activated partial thromboplastin time "NAPTT" test (Kingdon, H. S. et al., *Thromb. Diath. Haemorrh.*, 33, 617–631 (1975)). The results are summarized in Table 3 and were confirmed with Western blots. It can be seen that LiCl, KCl, NaCl, $MgCl_2$ and $Na_2SO_4$ are strongly factor-IX protecting at 1.0 14 concentration. It is noted that such effects can be demonstrated in both certain strongly salting in salts (Na or KSCN) and certain moderately salting out salts (KCl and $Na_2SO_4$).

The sodium acetate dialyzate showed considerably more factor IXa production than solutions of the other soluble salts although less factor IX activation and degradation were noted therein than would be expected using a 0.15M NaCl dialysis solution.

TABLE 3

Low Temperature Stability of Factor IX in 1M Concentrations of Various Salts

| Sample No. | 1M Salt | F.IX u/ml | F.IX$_a$ u/ml | NAPTT Dilution | % |
|---|---|---|---|---|---|
| 1 | Na Acetate | 25.5 | 0.130 | 1:10 | 45 |
| | | | | 1:100 | 82 |
| 2 | LiCl | 20.5 | 0.0294 | 1:10 | 62 |
| | | | | 1:100 | 91 |
| 3 | KCL | 20.5 | 0.0200 | 1:10 | 90 |
| | | | | 1:100 | 94 |
| 4 | MgCl$_2$ | 19.0 | 0.0016 | 1:10 | Did not clot |
| | | | | 1:100 | 106 |
| 5 | Na$_2$SO$_4$ | 20.5 | 0.0192 | 1:10 | 100 |
| | | | | 1:100 | 108 |
| 6 | NaCl | 21.0 | 0.0247 | 1:10 | 90 |
| | | | | 1:100 | 99 |
| Control | NaCl (thawed DEAE Sephadex eluate, without dialysis, after overnight storage.) | 21.0 | 0.0333 | 1:7 1:100 | 77 91 |

Example 7
Factor IX Purity As Validated By The Wessler Rabbit Stasis Assay.

This example demonstrates that factor IX purified in accord with the process of Example 1 does not cause unwanted coagulation as measured by the in vivo Wessler Rabbit Stasis Assay for thrombogenicity.

Factor IX preparations consisting of prior art DEAE Sephadex® eluates (diafiltered against physiologically isotonic buffer) and factor IX final products produced according to the practice of this invention (using anion exchange chromatography and held at high sodium chloride concentration prior to subsequent immunoaffinity chromatography) were injected in vivo into isolated, ligated sections of rabbit jugular veins according to the procedure of Wessler et al., *J. Appl. Physiol.* 14:943–946 (1959) to assess the formation of stasis thrombi.

Scoring was accomplished following the system of Wessler, et al. according to the size of the clot wherein a $^+4$ clot represents the largest size of clot which can normally be generated with thrombogenic materials in the size and type of vessel selected and $^+1$ is the smallest such clot which can be visibly detected. The results of the evaluations of the prior art compositions, and those of the present invention show that, in contrast to the use of compositions of the prior art, compositions of this invention show no adverse effects in vivo up to concentrations of factor IX on a per kg weight basis well beyond that which would be administered to a human hemophilia B patient. It is proposed that use of this assay in conjunction with analysis of SDS PAGE gels for 54 kDa peptides, and also the factor IXa assay (Example 3) is the best available method to predict of in vivo utility and safety of therapeutic factor IX preparations.

TABLE 4

Wessler Rabbit Stasis Assay for Thrombogenicity-Effect of Process Optimization on Thrombogenic Potential of Factor IX

| Lot Number | Potency (u/vl) | Rabbit Scores | | | | | | | | |
|---|---|---|---|---|---|---|---|---|---|---|
| | | 100 U/Kg | | | 200 U/Kg | | | 400 U/Kg | | |
| | | 1 | 2 | 3 | 1 | 2 | 3 | 1 | 2 | 3 |
| Prior Art Process for Factor IX | | | | | | | | | | |
| 1 | 1060 | $^+2$ | $^+3$ | $^+2$ | $^+2$ | $^+2$ | $^+2$ | $^+3$ | $^+4$ | $^+4$ |
| 2 | 500 | $^+1$ | $^+1$ | $^+2$ | $^+3$ | $^+2$ | $^+2$ | $^+3$ | $^+2$ | $^+2$ |
| 3 | 230 | $^+1$ | $^+1$ | $^+2$ | $^+1$ | $^+1$ | $^+1$ | $^+2$ | $^+1$ | $^+1$ |
| 4 | 255 | 0 | 0 | 0 | $^+2$ | $^+3$ | $^+3$ | $^+2$ | $^+3$ | $^+3$ |
| 5 | 1000 | 0 | 0 | 0 | $^+1$ | $^+2$ | $^+1$ | $^+2$ | $^+1$ | $^+2$ |
| 6 | 525 | 0 | 0 | 0 | ± | 0 | ± | $^+1$ | 0 | ± |
| Optimized Process For Monoclonal Factor IX | | | | | | | | | | |
| 7 | 590 | 0 | 0 | 0 | | | | 0 | 0 | 0 |
| 8 | 465 | 0 | 0 | 0 | | | | 0 | 0 | 0 |
| 9 | 540 | 0 | 0 | 0 | | | | 0 | $^+1$ | 0 |
| 10 | 490 | 0 | 0 | 0 | | | | 0 | 0 | $^+1$ |
| 11 | 520 | 0 | 0 | 0 | | | | 0 | 0 | 0 |

Example 8
Moderate Concentrations of Certain Salts are Effective to Protect Factor IX This example demonstrates that certain soluble salts are effective in protecting factor IX when used at lower concentrations than are generally needed for sodium chloride. Since use of prothrombin complex concentrate can lead to dangerous clinical effects, recently developed purification strategies incorporate additional separation steps in their protocols to further purify factor IX. Not all of these separation techniques (for example, certain column technologies) can be made to work in high molarity salt conditions. For example, factor IX may not adhere to a particular monoclonal antibody affinity column if the salt concentration is much above 0.5 Molar. Therefore it would be desirable to identify soluble salts which exhibit factor IX-protective effects when present at moderate molarity such as between about 0.4 and about 0.7 Molar, or below.

Accordingly, separate 5 ml aliquots of a sample of DEAE concentrate, the "stable factor IX-enriched fraction" produced via the protocol of Example 1 (containing also 1.0 M NaCl buffered at pH 7.0 with 10 mM sodium citrate) and which had been stored frozen at $^-80°$ C. were dialyzed overnight at 4° C. against 0.5 M solutions of NaCl, KCl, LiCl, Na$_2$SO$_4$ or MgCl$_2$. A citrate buffered 1.0 M NaCl dialyzate was used as a control. Assays for factor IX and factor IX$_a$ were then performed, and the samples were screened (FIG. 4) in the Western blot system.

Figure 4:
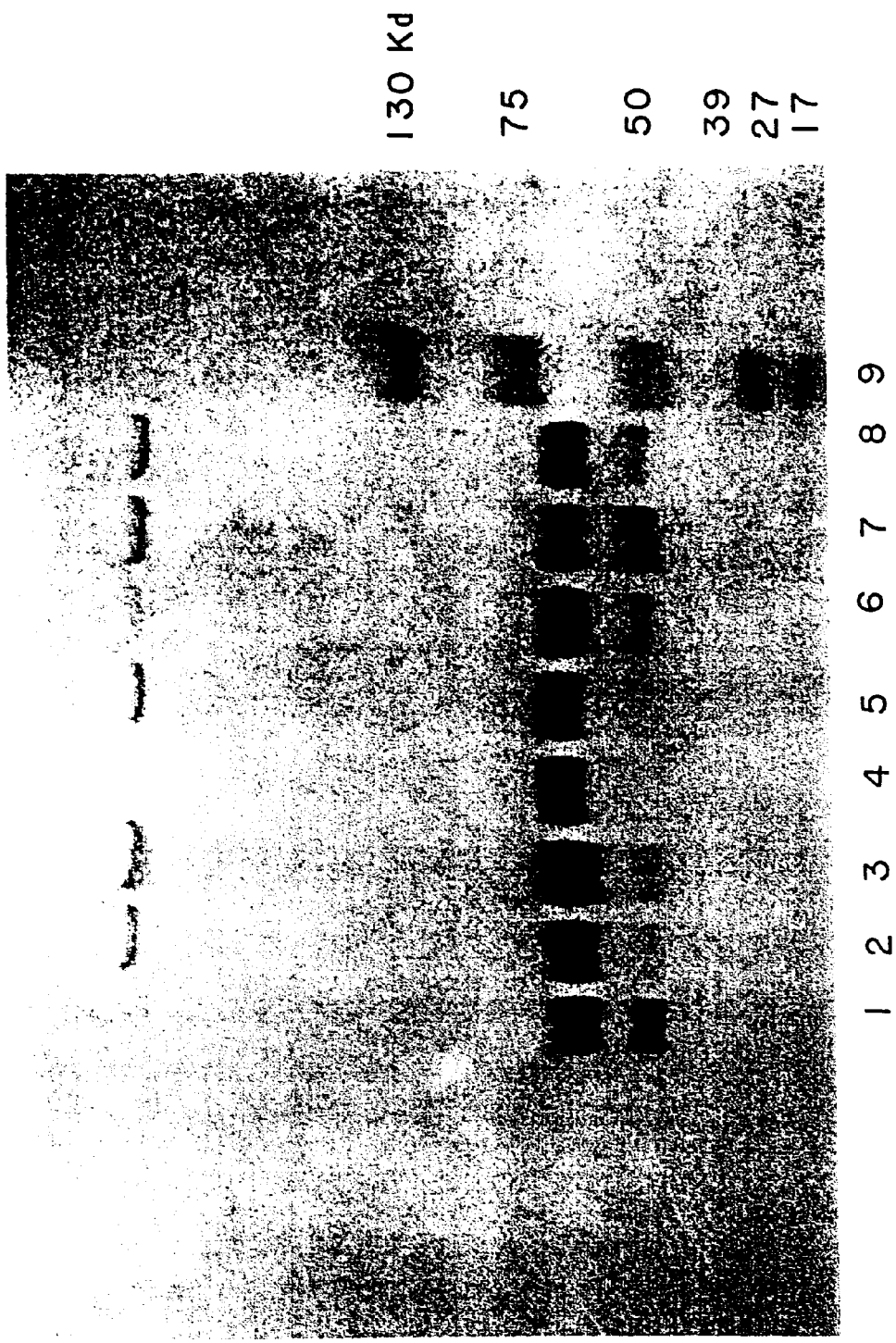
FIG. 4 is a Western blot showing levels of proteolysis of factor IX which occur at 4° C. in samples of factor IX-containing DEAE concentrate dialyzed against 0.5 Molar concentrations of different salts.

As is readily apparent from the blot in FIG. 4, buffered solutions of 0.5 M magnesium chloride (lane 3), sodium sulfate (lane 4), lithium chloride (lane 5) and potassium chloride (lane 6) each demonstrated factor IX stabilizing ability which is approximately equal to that of 1.0 M NaCl (lane 8) and considerably better than that of 0.5 M NaCl (lane 7). Lane 9 in FIG. 4 shows appropriate molecular weight markers. Lane 1 shows a control of DEAE concentrate made by the typical prior art process and dialyzed against isotonic buffer prior Lo freezing-resulting in a high content of 54 kDa degraded peptide; and lane 2 shows a sample of frozen DEAE concentrate produced as eluate from DEAE-Sephadex® resin maintained in high salt according to the practice of this invention.

What is claimed is:

1. A method of treating Christmas disease in a patient which comprises administering to such patient an effective amount of a therapeutic composition comprising an aqueous solution of purified factor IX having a specific activity of greater than about 50 units factor IX activity/mg protein, wherein the composition is capable of being stored for a period of time of about 2 weeks at a storage temperature up to 15–30° C. and wherein at the end of said period of storage the composition has a factor IX specific activity of greater than about 50 units and is free of factor $IX_a$, degraded forms of factor IX and/or active forms of other clotting factors in concentrations which would tend to cause detectable adverse clinical effects in a human when said composition is administered in a therapeutic dose.

2. A method according to claim 1 wherein the therapeutic composition has a factor IX-specific activity of greater than about 100 units/mg protein before and after said period of storage.

3. A method according to claim 2 wherein the therapeutic composition has a factor IX-specific activity of greater than about 194 units/mg protein before and after said period of storage.

4. A method according to claim 1 wherein in the therapeutic composition said purified factor IX is prepared by separating contaminating proteins in solution therewith by a purification process comprising at least two sequential separation steps, said purification process including the steps of (a) adding to said solution of factor IX and other proteins one or more organic or inorganic salts to a concentration of from about 0.7 to about 3 M and (b) maintaining said salt concentration in said solution between purification steps until the factor IX has been separated from the contaminating proteins which tend to activate factor IX to factor $IX_a$ and/or to degrade factor IX to peptides of altered length and/or conformation.

5. A method of treating Christmas disease in a patient which comprises administering to such patient an effective amount of a therapeutic composition comprising an aqueous solution of purified factor IX which is made using a method for purifying and preserving factor IX derived from human blood plasma or other source by separating factor IX from contaminating proteins which are in solution therewith by a purification process comprising at least two sequential separation steps, the improvement which comprises stabilizing factor IX in solution against activation to factor $IX_a$ or against degradation to peptides of altered length and/or conformation by the steps of (a) adding one or more soluble organic or inorganic salts to the factor IX-containing solution to a concentration of from about 0.7 to about 3 M prior to or during a first separation step, which concentration is sufficient to prevent or substantially minimize activation of or degradation of factor IX, but which concentration is insufficient to cause precipitation of, irreversible alterations in, or denaturation of the factor IX molecule, and (b) maintaining the salt(s) in the solution at said concentration until at least through commencement of a subsequent separation step in which the factor IX is separated from those impurities which tend to activate factor IX to factor $IX_a$ and/or to degrade factor IX to peptides of altered length and/or conformation.

6. A method of treating Christmas disease in a patient which comprises administering to such patient an effective amount of a therapeutic composition comprising an aqueous solution of purified fact-or IX which is made using a method of stabilizing factor IX which is derived from recombinant technology using bacterial, yeast or other cells against activation to factor $IX_a$ or against degradation to peptides of altered length and/or conformation which method comprises adding one or more soluble organic or inorganic salts to a solution containing said factor IX to a total concentration of salt of from about 0.7 to about 3 M, which concentration is sufficient to prevent or substantially minimize catalytic action by proteases upon factor IX, but at a total concentration of said salt or salts insufficient to cause precipitation of, irreversible alterations in, or denaturation of the factor IX molecule.

7. A composition which comprises a lyophilized powder, solution, suspension, or frozen solution or suspension, of factor IX having a specific activity of factor IX above about 50 units/mg of protein and which includes, on a percent by weight of protein basis, no more than about 0.1% of factor $IX_a$, or no more than about 10% in total of one or more factor IX degradation peptides having molecular weights from approximately 40 to approximately 65 kDa.

8. The composition of claim 7 wherein said specific activity of factor IX is above about 194 units/mg of protein.

9. The composition of claim 7 wherein the composition is capable of being stored for a period of time of about 2 weeks at a storage temperature up to 15–30° C. and wherein at the end of said period of storage the composition has a factor IX specific activity of greater than about 50 units/mg of protein.

* * * * *